(12) United States Patent
Kandula (10) Patent No.: US 8,283,375 B2
(45) Date of Patent: Oct. 9, 2012

(54) 2, 6 XYLIDINE DERIVATIVES FOR THE TREATMENT OF PAIN

(75) Inventor: Mahesh Kandula, Medapadu (IN)

(73) Assignee: Krisani Biosciences (P) Ltd., Hyderabad (IN)

( * ) Notice: Subject to any disclaimer, the term of this patent is extended or adjusted under 35 U.S.C. 154(b) by 0 days.

(21) Appl. No.: 13/418,836

(22) Filed: Mar. 13, 2012

(65) Prior Publication Data

US 2012/0172421 A1 Jul. 5, 2012

Related U.S. Application Data (60) Provisional application No. 61/524,430, filed on Aug. 17, 2011.

(51) Int. Cl.
*A01N 43/02* (2006.01)
*A01N 43/06* (2006.01)
*A01N 43/12* (2006.01)
*A61K 31/38* (2006.01)

(52) U.S. Cl. .................. 514/430; 514/438; 514/443

(58) Field of Classification Search ............... 514/430, 514/438, 443
See application file for complete search history.

(56) References Cited

OTHER PUBLICATIONS

Christopher J. LaBuda et al. Pharmacological evaluation of the selective spinal nerve ligation model of neuropathic pain in the rat, Journal of Neuroscience Methods 144 (2005) 175-181.

*Primary Examiner* — Yong Chong
(74) *Attorney, Agent, or Firm* — Geeta Kadambi; Riddhi IP LLC (57) ABSTRACT

The disclosure herein provides a compound of formula 1. The disclosure also provides a method of synthesizing the compound of formula 1. The compound of formula 1 or its pharmaceutical acceptable salts, as well as polymorphs, solvates, and hydrates thereof may be formulated as pharmaceutical composition. The pharmaceutical composition of compound of formula 1 or the final compound may be formulated for non-invasive peroral, topical (example transdermal), enteral, transmucosal, targeted delivery, sustained release delivery, delayed release, pulsed release and parenteral methods. Such compositions may be used to treat chronic pain manifested with chronic diseases or its associated complications. The compound may also be offered as a kit.

10 Claims, 9 Drawing Sheets

2, 6 XYLIDINE DERIVATIVES FOR THE TREATMENT OF PAIN

CROSS REFERENCE TO RELATED APPLICATIONS

This application claims priority to U.S. patent application Ser. No. 13/228,909, filed on 9 Sep. 2011 and U.S. Provisional Application 61/524,430, filed on 17 Aug. 2011. These applications are hereby incorporated by this reference in their entireties for all of its teachings.

FIELD OF THE INVENTION

This disclosure generally relates to a compound made of 2,6 xylidine derivative, method of synthesizing the compound and method of treating pain using the compound of formula 1. More particularly, this disclosure relates to treating subjects suffering from neuropathic pain with pharmaceutically acceptable dose of compound of formula 1 or the prodrug of the compound formula 1.

BACKGROUND

Pain attributed to tissue injury is mainly caused by inflammation. The mechanism of peripheral inflammation includes local liberation of mediators released by cell lysis, inflammatory cells, and nerve endings. Nerve roots are vulnerable to compression (e.g., compressive radiculopathy, infections, and tumors). If the lesion is proximal to the dorsal root ganglion, there may be abnormality of the central axons but not necessarily of the peripheral axons. Therefore, tests aimed at the peripheral axons will not detect the injury in those situations. Likewise, complete degeneration of the axon is not necessary to produce clinical symptoms: lesions may be in the form of perinodal retraction of myelin or frank demyelination. Demyelination with emphatic spread of action potentials between adjacent axons is believed to underlie bursts of lacerating pain because the action potentials transmitted along a few fibers can inappropriately spread many other axons.

Chronic pain is a significant global health, economic and social problem. Complex regional pain syndrome is one of the most severe and mysterious neuropathic pain syndromes. The clinical symptoms of complex regional pain syndrome always include pain, hyperalgesia, and allodynia.

Managing acute and chronic pathology of pain often relies on the addressing underlying pathology and symptoms of the disease. There is currently a need in the art for new compounds for treatment of acute and chronic pain.

SUMMARY OF DISCLOSURE

The instant disclosure presents a compound of formula 1, method of synthesizing the compound of formula 1 and using the compound of formula 1 for treating a mammal suffering with pain. In one embodiment a pharmaceutical composition comprising one or more compounds of formula 1 or intermediates thereof with one or more of pharmaceutically acceptable carriers, vehicles or diluents are disclosed and used for treating pain. In another embodiment, these compounds may be used in the treatment of pain and related complications.

In one embodiment, a compound of formula 1 is disclosed.

Formula 1

In another embodiment, the compounds of formula 1 or administering formula 1 in a pharmaceutically acceptable salt form to a patient and/or a mammal is disclosed.

In another embodiment, the compound of formula 1 contains thioctic acid, enantiomers of thioctic acid in a R(+)-stereoisomeric form only.

In one embodiment the pharmaceutically acceptable amount of the compound of formula 1 may be administered, but not limited to, as an injection. In another embodiment, administration of the formula 1 as a drug may include peroral, topical, transmucosal, inhalation, targeted delivery and sustained release formulations. In one embodiment, the formula 1 may be administered as a treatment method for pain associated with various diseases.

Herein the disclosure also provides a kit comprising the compound of formula 1 and/or the pharmaceutically acceptable form of compound of formula 1. The kit may comprise instructions for use the compound of formula 1 and/or pharmaceutically acceptable form of compound of formula 1 to be used as a treatment for pain or related complications.

The disclosure also discloses a pharmaceutical compound comprising a pharmaceutically acceptable carrier and the compound of formula 1 herein.

The compound described herein has several uses. The present disclosure provides, for example, methods of treating a patient suffering from pain manifested from chronic diseases or disorders, Hematological, Orthopedic, Cardiovascular, Renal, Skin, Neurological, Metastasis (cancer) or Ocular complications. The compounds may also be used in biochemical research, for example in studying and modulating neural voltage transmission and homeostasis and also neural channels.

The compound, composition, formulation, method of synthesis, and treatment disclosed herein may be implemented in any means for achieving various aspects, and may be executed in a form suitable for the mammal. Other features will be apparent from the accompanying figures and detailed description that follows.

BRIEF DESCRIPTION OF FIGURES

Example embodiments are illustrated by way of example and not limitation in the figures of the accompanying drawings, in which like references indicate similar elements and in which.

DETAILED DESCRIPTION

According to one embodiment, compound of formula 1 and its physiologically compatible acid-addition salts are used for the pharmaceutical preparations for the treatment and/or prophylaxis of pain, more specifically neuropathic pain.

As used herein, the following terms and phrases shall have the meanings set forth below. Unless defined otherwise, all technical and scientific terms used herein have the same meaning as commonly understood to one of ordinary skill in the art.

The compounds of the present disclosure can be present in the form of pharmaceutically acceptable salts. The compounds of the present disclosure can also be present in the form of pharmaceutically acceptable esters (i.e., the methyl and ethyl esters of the acids of formula 1 to be used as prodrugs). The compounds of the present disclosure can also be solvated, i.e. hydrated.

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable minor images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein, the term "pain" refers to an unpleasant sensory and emotional experience associated with actual or potential tissue damage caused by or resulting in stimulation of nociceptors in the peripheral nervous system, or by damage to or malfunction of the peripheral or central nervous systems and neural voltage channel transmission. Pain related diseases or disorders includes such as Cancer (chemotherapy and surgery related), Neurologic (bradykinesia, rigidity, tremor, ataxia, dyskinesia, dysarthria, seizures, neuropathic pain), Psychiatric (behavioral disturbances, cognitive impairment, psychosis), Ophthalmologic (dry eye, cataracts), Hematologic (haemolysis, coagulopathy), Renal (renal tubular defects, diminished glomerular filtration, nephrolithiasis), Cardiovascular (cardiomyopathy, arrhythmias, conduction disturbances, autonomic dysfunction), Musculoskeletal (osteomalacia, osteoporosis, degenerative joint diseases), Gastrointestinal (cholelithiasis, pancreatitis, bacterial peritonitis), Surgery or amputation related or any other medical condition, is well understood in the art, and includes administration of a compound which reduces the frequency of, or delays the onset of, symptoms of a medical condition in a subject relative to a subject which does not receive the compound.

The term "polymorph" as used herein is art-recognized and refers to one crystal structure of a given compound.

"Residue" is an art-recognized term that refers to a portion of a molecule. For instance, a residue of thioctic acid may be: dihydrolipoic acid, bisnorlipoic acid, tetranorlipoic acid, 6,8-bismethylmercapto-octanoic acid, 4,6-bismethylmercapto-hexanoic acid, 2,4-bismethylmeracapto-butanoic acid, 4,6-bismethylmercapto-hexanoic acid.

The phrases "parenteral administration" and "administered parenterally" as used herein refer to modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intra-articular, subcapsular, subarachnoid, intraspinal and intrastemal injection and infusion.

A "patient," "subject," or "host" to be treated by the subject method may mean either a human or non-human animal, such as primates, mammals, and vertebrates.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluents, solvent or encapsulating material involved in carrying or transporting any subject composition, from one organ, or portion of the body, to another organ, or portion of the body. Each carrier must be "acceptable" in the sense of being compatible with the other ingredients of a subject compound and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "polymorph" as used herein is art-recognized and refers to one crystal structure of a given compound.

The term "prodrug" is intended to encompass compounds that, under physiological conditions, are converted into the therapeutically active agents of the present disclosure. A common method for making a prodrug is to include selected moieties that are hydrolyzed under physiological conditions to reveal the desired molecule. In other embodiments, the prodrug is converted by an enzymatic activity of the host animal. The present disclosure also contemplates prodrugs of the compounds disclosed herein, as well as pharmaceutically acceptable salts of said prodrugs.

The term "prophylactic or therapeutic" treatment is art-recognized and includes administration to the host of one or more of the subject compounds. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e., it is intended to diminish, ameliorate, or stabilize the existing unwanted condition or side effects thereof).

The term "treating" is art-recognized and includes preventing a disease, disorder or condition from occurring in an animal which may be predisposed to the disease, disorder and/or condition but has not yet been diagnosed as having it; inhibiting the disease, disorder or condition, e.g., impeding its progress; and relieving discomfort from the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain. The term "treating", "treat" or "treatment" as used herein includes curative, preventative (e.g., prophylactic), adjunct and palliative treatment.

The phrase "therapeutically effective amount" is an art-recognized term. In certain embodiments, the term refers to an amount of a salt or compound disclosed herein that produces some desired effect at a reasonable benefit/risk ratio applicable to any medical treatment. In certain embodiments, the term refers to that amount necessary or sufficient to eliminate or reduce medical symptoms for a period of time. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

In certain embodiments, the pharmaceutical compositions described herein are formulated in a manner such that said compounds will be delivered to a patient in a therapeutically effective amount, as part of a prophylactic or therapeutic treatment. The desired amount of the compound to be administered to a patient will depend on absorption, inactivation, and excretion rates of the drug as well as the delivery rate of the salts and compounds from the subject compounds. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions.

Additionally, the optimal concentration and/or quantities or amounts of any particular salt or compound may be adjusted to accommodate variations in the treatment parameters. Such treatment parameters include the clinical use to which the preparation is put, e.g., the site treated, the type of patient, e.g., human or non-human, adult or child, and the nature of the disease or condition.

The term "solvate" as used herein, refers to a compound formed by solvation (e.g., a compound formed by the combination of solvent molecules with molecules or ions of the solute).

When used with respect to a pharmaceutical composition or other material, the term "sustained release" is art-recognized. For example, a subject compound which releases a substance over time may exhibit sustained release characteristics, in contrast to a bolus type administration in which the entire amount of the substance is made biologically available at one time. For example, in particular embodiments, upon contact with body fluids including blood, spinal fluid, mucus secretions, lymph or the like, one or more of the pharmaceutically acceptable excipient may undergo gradual or delayed degradation (e.g., through hydrolysis) with concomitant release of any material incorporated therein, e.g., an therapeutic and/or biologically active salt and/or compound, for a sustained or extended period (as compared to the release from a bolus). This release may result in prolonged delivery of therapeutically effective amounts of any of the therapeutic agents disclosed herein.

The phrases "systemic administration," "administered systemically," "peripheral administration" and "administered peripherally" are art-recognized, and include the administration of a subject compound, therapeutic or other material at a site remote from the disease being treated. Administration of an agent directly into, onto, or in the vicinity of pain sensation of the disease being treated, even if the agent is subsequently distributed systemically, may be termed "local" or "topical" or "regional" administration, other than directly into the central nervous system, e.g., by subcutaneous administration, such that it enters the patient's system and, thus, is subject to metabolism and other like processes.

Generally, in carrying out the methods detailed in this disclosure, an effective dosage for the compounds of Formulas 1 is in the range of about 0.3 mg/kg/day to about 60 mg/kg/day in single or divided doses, for instance 1 mg/kg/day to about 50 mg/kg/day in single or divided doses. The compounds of Formulas I may be administered at a dose of, for example, less than 2 mg/kg/day, 5 mg/kg/day, 10 mg/kg/day, 20 mg/kg/day, 30 mg/kg/day, or 40 mg/kg/day. Compounds of Formula 1 may also be administered to a human patient at a dose of, for example, between 50 mg and 1000 mg, between 100 mg and 800 mg, or less than 1000, 900, 800, 700, 600, 500, 400, 300, 200, 150 or 100 mg per day. In certain embodiments, the compounds herein are administered at an amount that is less than 95%, 90%, 80%, 70%, 60%, 50%, 40%, 30%, 20%, or 10% of the compound of formula 1 required for the same therapeutic benefit.

In some cases, it may be desirable to administer in the form of a kit, it may comprise a container for containing the separate compounds such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Compound of formula 1 is disclosed as follows: In one embodiment, a compound of formula 1 is disclosed.

Formula 1

In certain embodiments, the compound of formula 1 or pharmaceutically acceptable salts thereof, Formula 1

Figure 1:
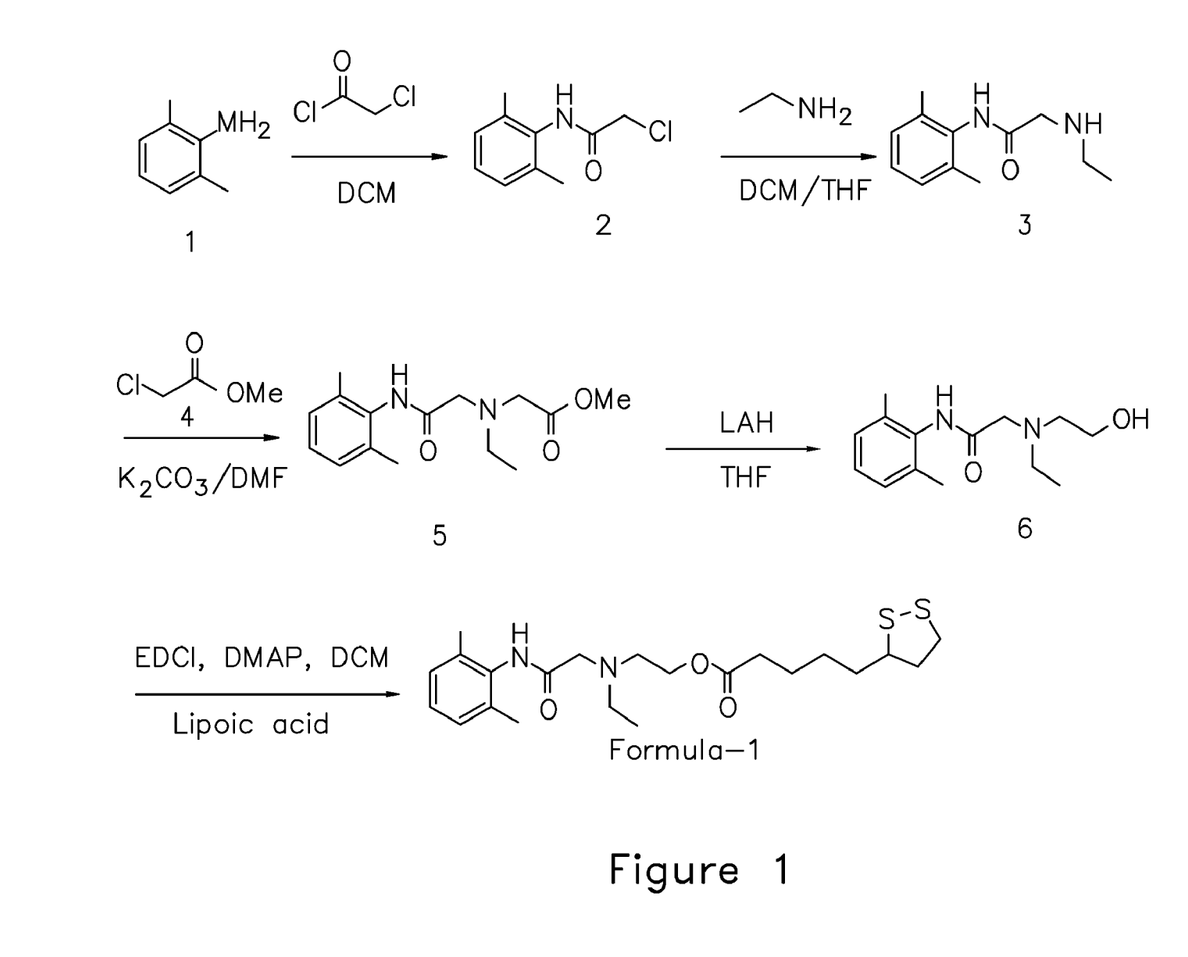
FIG. 1 illustrates the synthesis of a compound of formula 1.
Figure 2A:
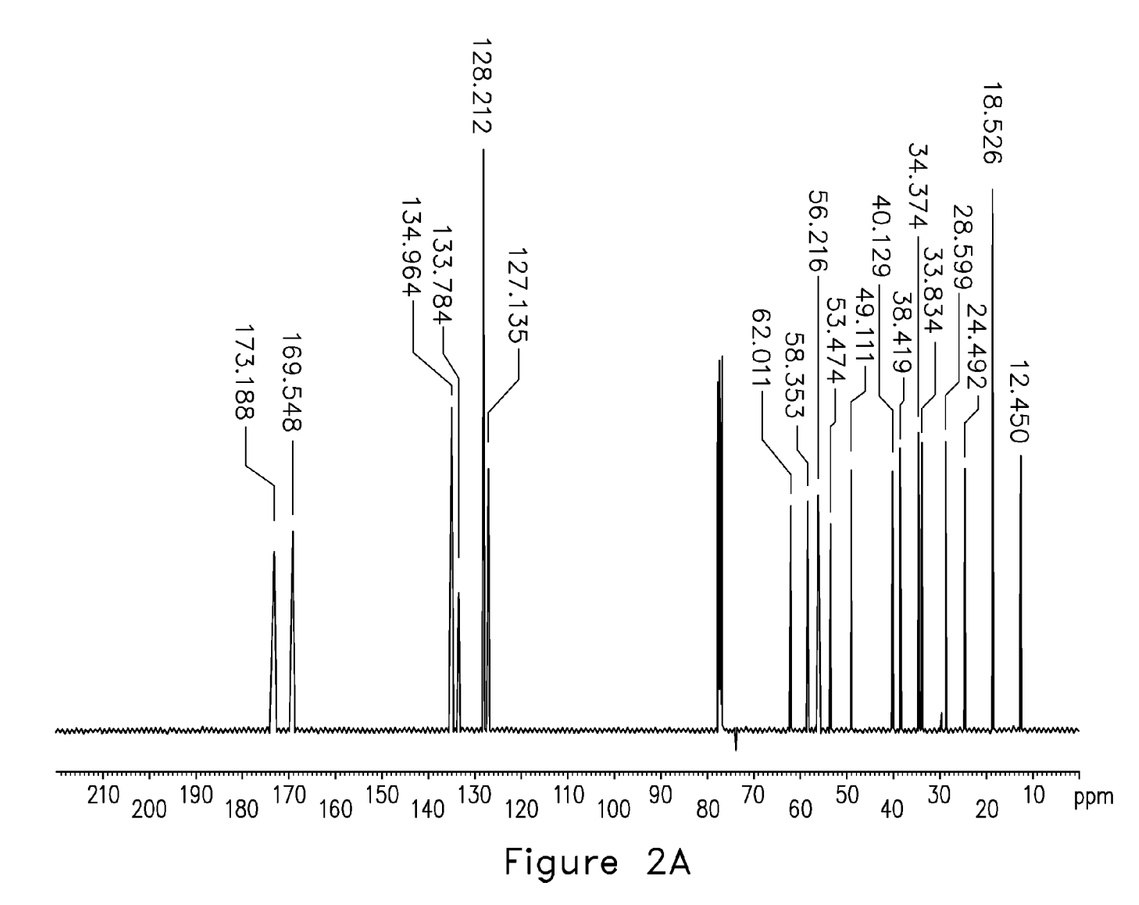
FIG. 2A-2D shows the C13-NMR results for formula 1.
Figure 2B:
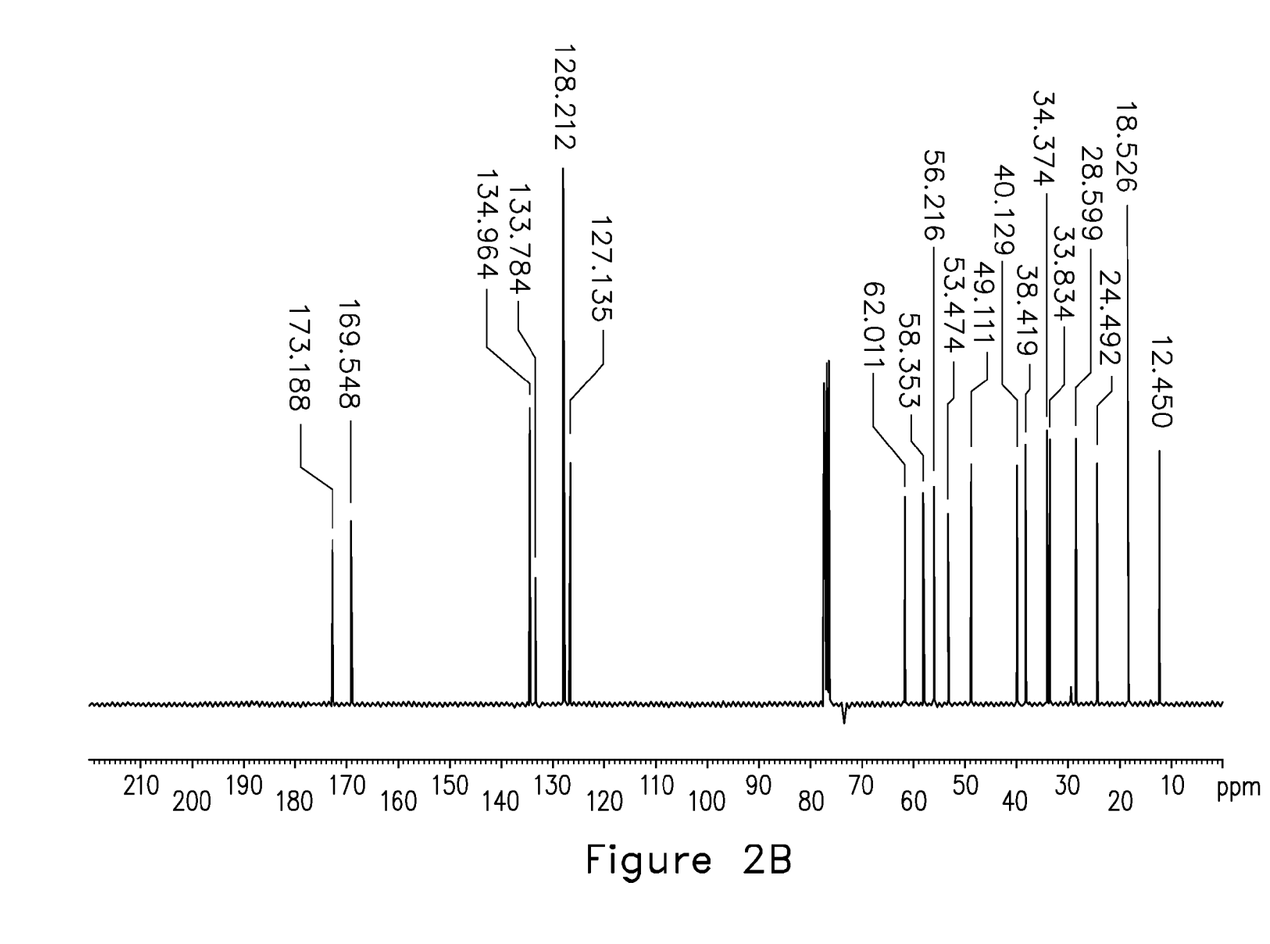
Figure 2C:
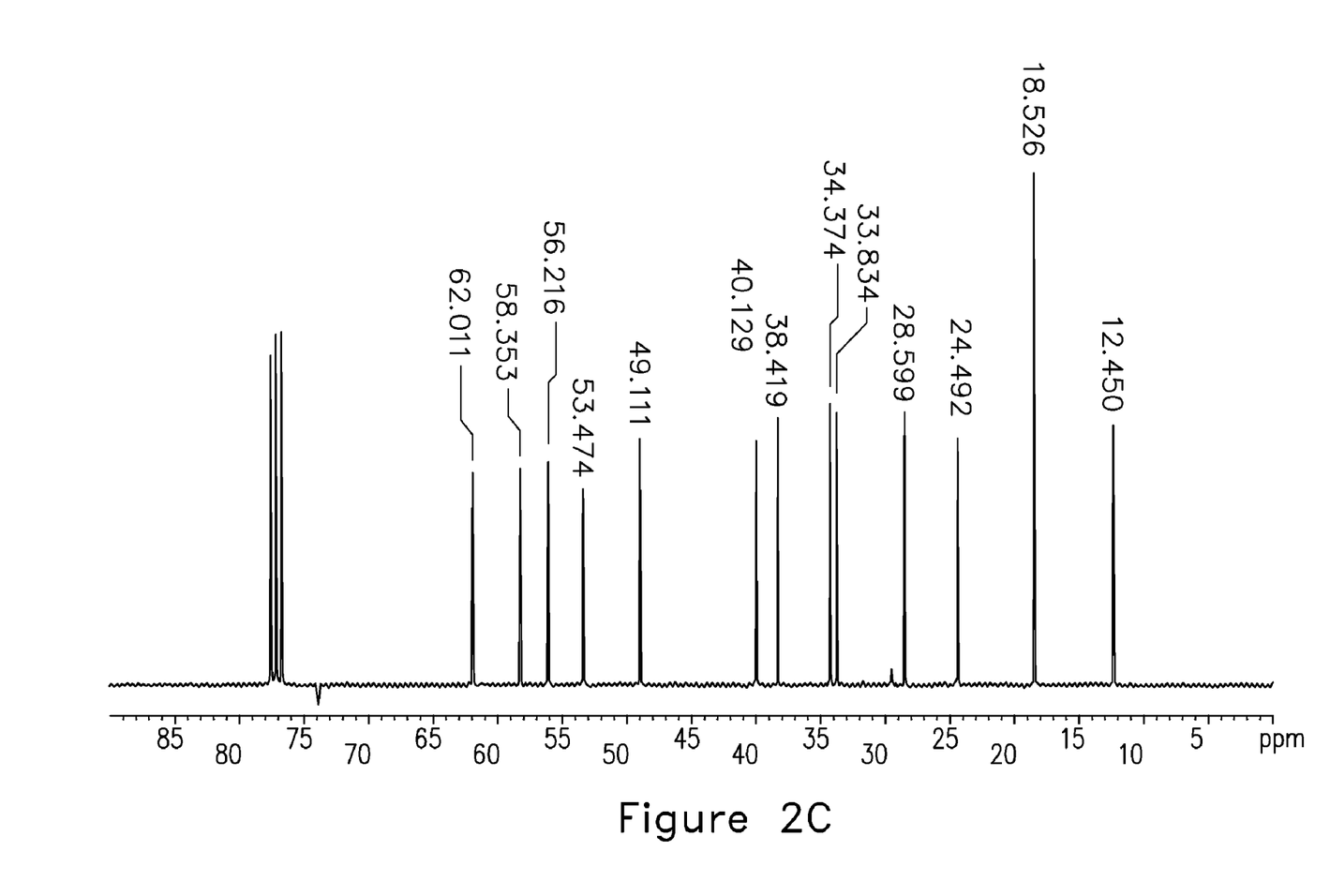
Figure 2D:
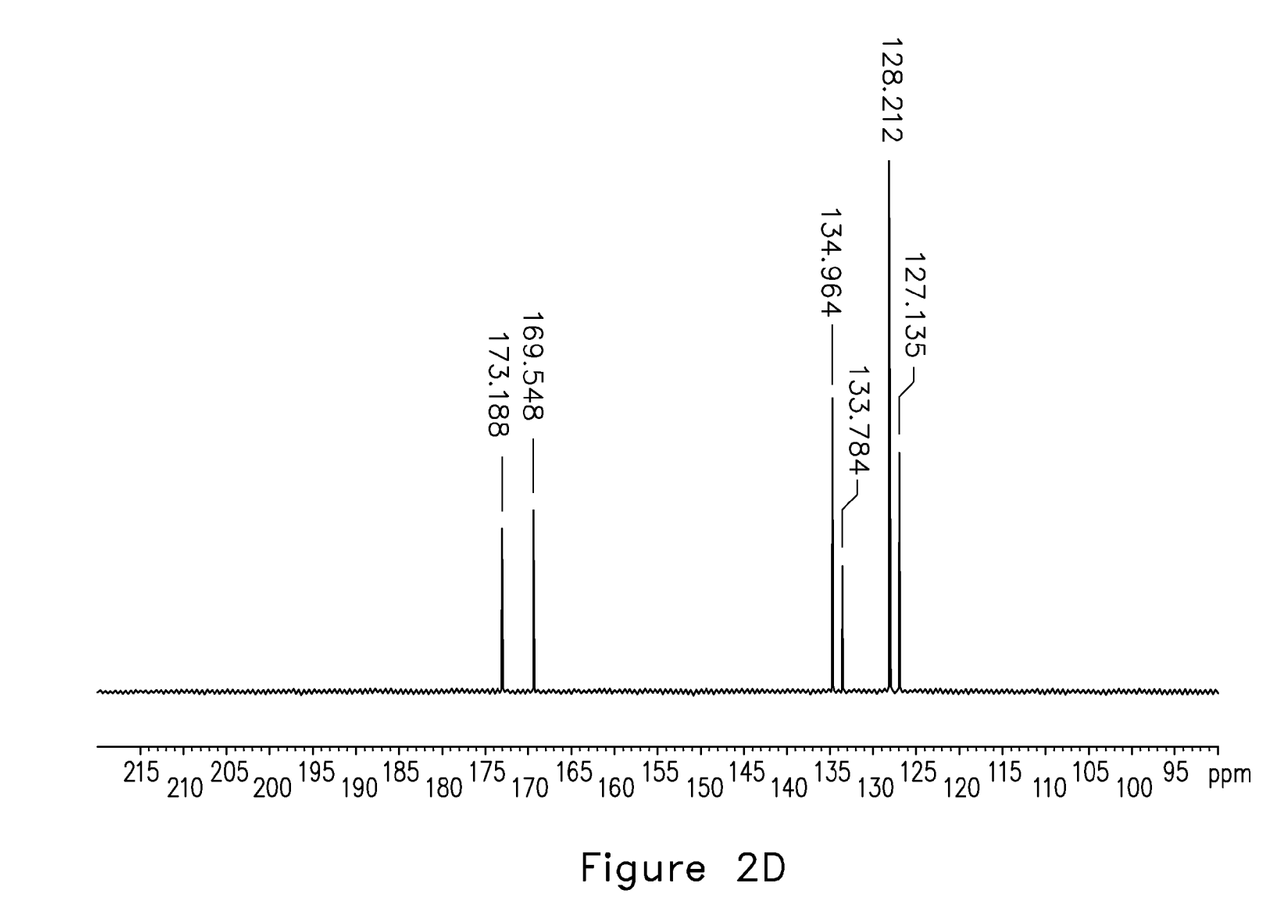
Figure 2E:
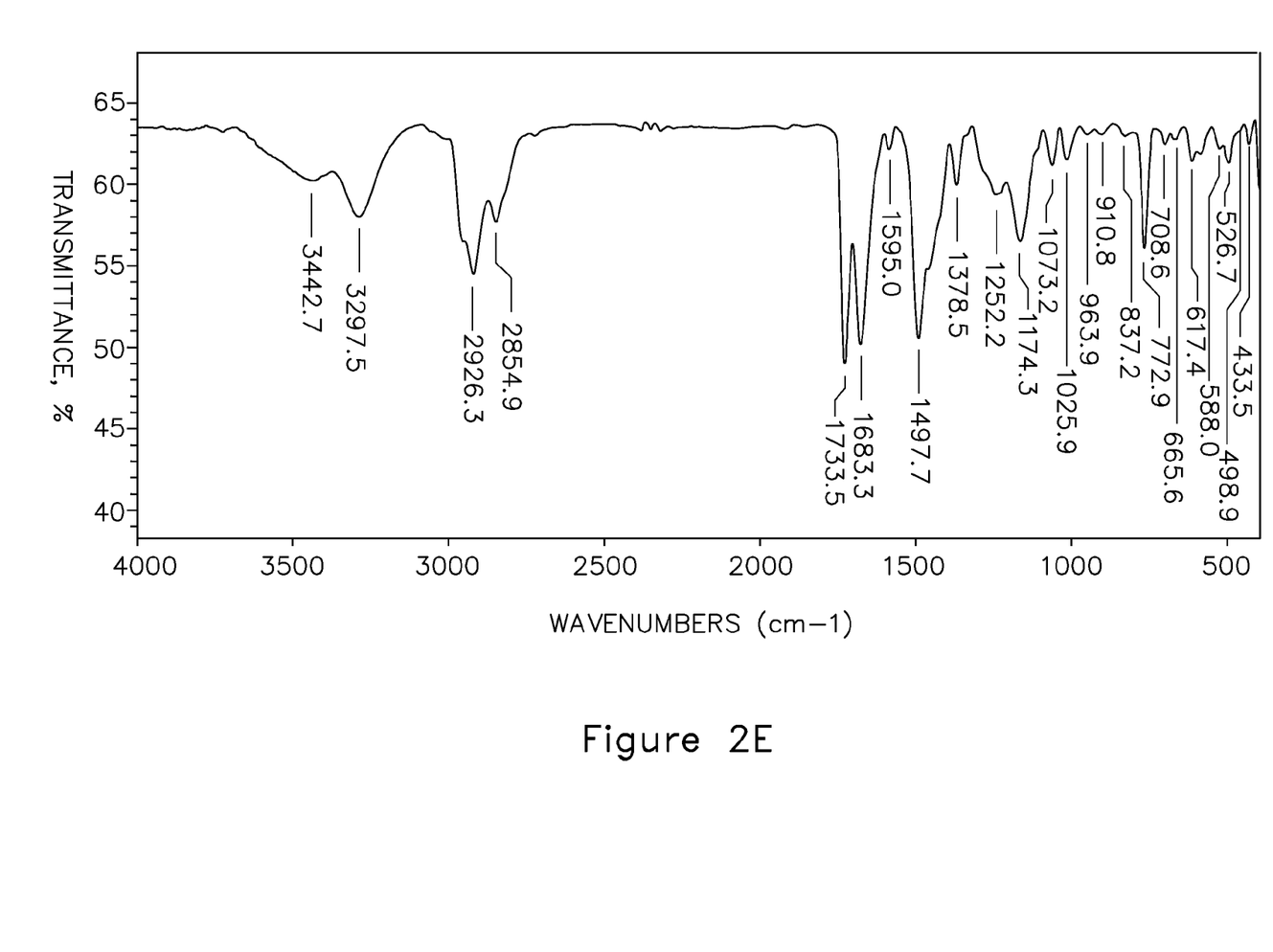
FIG. 2E shows the graph for Infra red Report for compound of formula 1.

Method of Synthesis of the Compound of Formula 1:

Step-1: Synthesis of Compound 2:

Procedure: To the solution of 2, 6 xylidine 1 (50.0 g, 41.26 mmol; 1.0 eq) in 1.0 L of Dichloromethane and then add chloroacetyl chloride (51.26 g, 45.38 mmol; 1.0 eq) drop wise for 30 min at 0° C. The reaction mixture is brought to room temperature & left for stifling for overnight. On completion of the reaction (monitored by TLC), the reaction mixture was washed with water (1.0 L), followed by brine solution (0.5 L), the organic layer was dried over anhydrous Na$_2$SO$_4$ and evaporated under reduced pressure to get product 2 which was recrystalized in hexane (1 L) and the solid filtered to yield 70 g (86.12%) of compound 3 as a white solid.

TABLE 1

$^1$H NMR (DMSO-d$_6$, 300 MHz)

| δ | splitting pattern & J value | Protons | Group |
|---|---|---|---|
| 9.64 | s | 1H | NH |
| 7.08 | s | 3H | ArH |
| 4.28 | s | 2H | CH$_2$Cl |
| 2.14 | s | 6H | 2xCH$_3$ |

Step-2: Synthesis of Compound 3:

Procedure: To the ethyl amine solution in THF (150 ml) was added compound 2 (70.0 g, 35.53 mmol, 1.0 eq) in 700 ml of THF drop wise at room temperature & left for stifling for 4 h. Reaction completion (monitored by TLC), the reaction mixture was concentrated under reduced pressure. Recystalization was done in ethyl acetate (1 L) and the solid was filtered & dried to yield 80 g (91.14%) of compound 3 as a white solid.

TABLE 2

$^1$H NMR (CD$_3$OD, 300 MHz)

| δ | splitting pattern & J value | Protons | Group |
|---|---|---|---|
| 7.12 | m | 3H | ArH |
| 4.10 | s | 3H | CH$_3$CH$_2$N |
| 3.17 | qt, J = 7.31 Hz | 2H | COCH$_2$ |
| 2.24 | s | 6H | 2xCH$_3$ |
| 1.36 | t, J = 7.31 Hz | 3H | CH$_3$CH$_2$N |

Step-3: Synthesis of Compound 5:

Procedure: To the solution of compound 3 (80.0 g, 38.83 mmol, 1.0 eq) in 800 mL of N,N-Dimethylformamide, potassium carbonate (100.0 g, 72.37 mmol, 1.86 eq) & methyl chloroacetate (47.54 g, 43.61 mmol, 1.0 eq) was added simultaneously at room temperature & left for stifling for 24 h. Reaction completion (monitored by TLC), the reaction mixture partitioned between ethyl acetate (1 L) and water (1 L), followed by washing organic layer with brine solution (1 L), the organic layer was dried over anhydrous Na$_2$SO$_4$ and evaporated under reduced pressure. The reaction residue purified by column chromatography eluting with 40% ethyl acetate in hexane to provide compound 5 100 g (92.6%) as a viscous liquid.

TABLE 3

$^1$H NMR (CDCl$_3$, 300 MHz)

| δ | splitting pattern & J value | Protons | Group |
|---|---|---|---|
| 9.03 | s | 1H | NH |
| 7.09 | s | 3H | ArH |
| 3.75 | s | 3H | OCH$_3$ |
| 3.50 | s | 2H | NCH$_2$ |
| 3.40 | s | 2H | NCH$_2$ |
| 2.81 | q, J = 7.16 Hz | 2H | NCH$_2$CO |
| 2.24 | s | 6H | 2xCH$_3$ |
| 1.16 | t, J = 7.16 Hz | 3H | CH$_3$CH$_2$N |

Step-4: Synthesis of Compound 6:

Procedure: Lithium aluminum hydride (36.4 g, 95.7 mmol, 2.5 eq) was taken in three neck RB (2 L) flask under nitrogen atmosphere & cooled to 0° C., dropwise tetra hydrofuran (500 mL) was added, then a solution of compound 5 (140.0 g, 50.35 mmol, 1.0 eq) in 100 L of THF was added drop wise at 0° C. temperature & left for stirring for 2 h at RT. Reaction completion was monitored by TLC, and the reaction mixture quenched with saturated ammonium chloride (200 mL), filtered through celite bed & filtrate was extracted with ethyl acetate (1.0 L), the organic layer was dried over anhydrous $Na_2SO_4$ and evaporated under reduced pressure to yield 45 g (35.77%) of compound 6 as a viscous liquid.

TABLE 4

$^1$H NMR ($CDCl_3$, 300 MHz)

| δ | splitting pattern & J value | Protons | Group |
|---|---|---|---|
| 8.88 | s | 1H | NH |
| 7.08 | s | 3H | ArH |
| 3.72 | t, J = 5.39 Hz | 3H | $CH_2O$ |
| 3.29 | s | 2H | $NCH_2CO$ |
| 2.72-2.68 | m | 4H | $CH_3CH_2N$, $CH_2N$ |
| 2.21 | s | 6H | $2xCH_3$ |
| 1.13 | t, J = 7.11 Hz | 3H | $CH_5CH_2N$ |

Step-5: Synthesis of Compound Formula 1:

Procedure: To a stirred solution of compound 6 (45 g, 18.0 mmol; 1.0 eq) and R-(+)-Lipoic acid (37.08 g, 18.0 mmol; 1.0 eq) in DCM (900 mL; LR grade); EDC.HCl (51.75 g, 27.0 mmol; 1.5 eq) and DMAP (21.99 g, 18.0 mmol; 1.0 eq) were added at RT and the reaction mixture was allowed to stir for 24 h at RT. Reaction was monitored by TLC. On completion of the reaction, the reaction mixture was diluted with DCM (200 mL), washed with water (2×300 mL) followed by brine solution (300 mL) and dried over anhydrous $Na_2SO_4$ and evaporated under reduced pressure. The crude was purified by column chromatography over 100-200 mesh silica gel by using 40% ethyl acetate-pet ether. Yield 51.0 g (62.27%) of compound formula 1 as a pale yellow semi-solid.

TABLE 5

$^1$H NMR ($CDCl_3$, 300 MHz) δ:

| δ | splitting pattern & J value | Protons | Group |
|---|---|---|---|
| 8.84 | s | 1H | NH |
| 7.10 | s | 3H | ArH |
| 4.23 | t, J = 5.4 Hz | 2H | $OCH_2$ |
| 3.55-3.45 | m | 1H | CHS |
| 3.22-3.05 | m | 2H | $CH_2S$ |
| 2.91 | t, J = 5.42 Hz | 2H | $CH_2N$ |
| 2.75 | q, J = 7.10 Hz | 2H | $CH_3CH_2N$ |
| 2.49-2.38 | m | 1H | $CH_2$ |
| 2.61 | t, J = 6.56 Hz | 2H | $CH_2CO$ |
| 2.23 | s | 6H | $2xCH_3$ |
| 1.92-1.80 | m | 1H | $CH_2$ |
| 1.60-1.32 | m | 6H | $3xCH_2$ |
| 1.15 | t, J = 7.10 Hz | 3H | $CH_3$ |

C NMR Studies:

TABLE 6

$^{13}$C NMR ($CDCl_3$, 300 MHz) δ:

| δ | Carbon position | Group |
|---|---|---|
| 173.18 | C8 | CO |
| 169.55 | C14 | NCO |
| 134.96 | C16, C20 | PhC |
| 133.78 | C15 | PhC |
| 128.21 | C17, C19 | PhCH |
| 127.13 | C18 | PhCH |
| 62.01 | C9 | $OCH_2$ |
| 58.35 | C13 | NCH2CO |
| 56.21 | C3 | CHS |
| 53.37 | C10 | CH2N |
| 49.11 | C11 | NCH2 |
| 40.12 | C1 | $CH_2S$ |
| 38.41 | C2 | $CH_2$ |
| 34.37 | C7 | $CH_2CO$ |
| 33.83 | C4 | $CH_2$ |
| 28.59 | C5 | $CH_2$ |
| 24.49 | C6 | $CH_2$ |
| 18.52 | C22, C21 | $CH_3$ |
| 12.45 | C12 | $NCH_2CH_3$ |

Method of Treatment, Testing and Results Using the Final Compound

Figure 3:
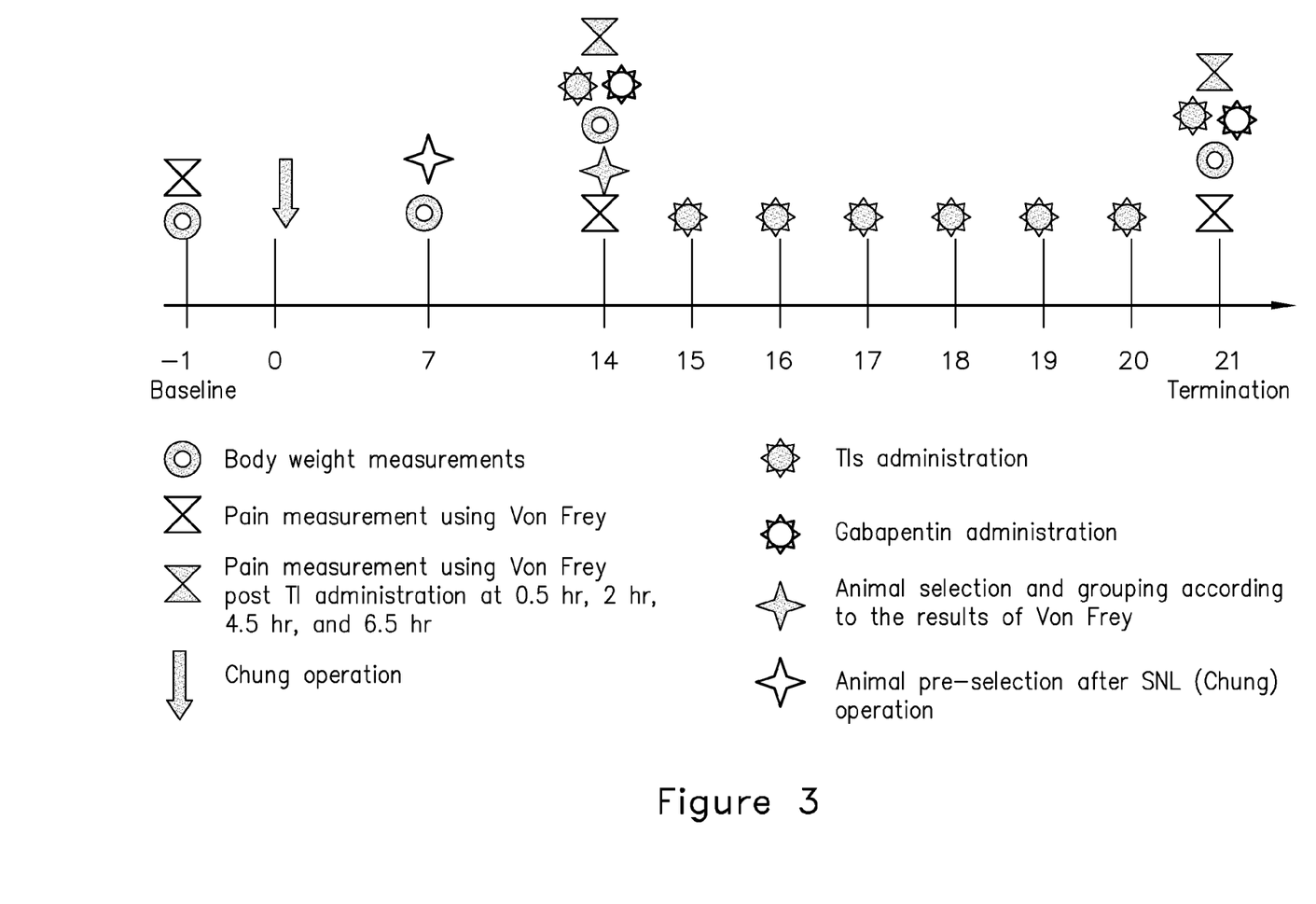
FIG. 3 displays the drug application regiment for 21 days duration.

Experimental animals were male SD rats with a starting weight of 230-250 grams. Total number of animals were n=90 for surgery and n=60 after selection. The animals were caged in groups of 3 in a temperature and humidity controlled area. They were maintained on a 12 hr light/dark cycle and had ad libitum access to food and water.

sure. Three types of experimental groups were formed. Different types of chemicals such as Vehicle and Control were used to determine the efficacy of the chemicals as well comparison of the instant disclosed compound of formula 1, with a positive control was performed. The final compound of the instant disclosure was administered at 100 mg/kg and 150 mg/kg body weight as two different groups. The Gabapentin was administered at 150 mg/kg body weight.

TABLE 7

Test Groups and dose regiment:

| Group No. | Group Size | Test Item | Route | Dose (mg/kg) | Volume (ml/kg) | Dosing Regime | Testing Regime |
|---|---|---|---|---|---|---|---|
| 1 | N = 10 | Blank | IP | 0 mg/kg | 5 ml/kg | Once daily starting on study day 14 through study day 21 | Von Frey testing at 0.5 hours, at 2 hours and at 4.5 hours after dosing on study days 14 and 21 |
| 2 | N = 10 | KRB-5/Pre | IP | 150 mg/kg | 5 ml/kg | Once daily starting on study day 14 through study day 21 | Von Frey testing at 0.5 hours, at 2 hours and at 4.5 hours after dosing on study days 14 and 21 |
| 3 | N = 10 | Gabapentin (Positive Control) | IP | 150 mg/kg | 5 ml/kg | On study days 14 and 21 2 hours prior to Von Frey testing | Von Frey testing at 0.5 hours, at 2 hours and at 4.5 hours after dosing on study days 14 and 21 |
| 4 | N = 10 | KRB-5/Pre | IP | 100 mg/kg | 5 ml/kg | Once daily starting on study day 14 through study day 21 | Von Frey testing at 0.5 hours, at 2 hours and at 4.5 hours after dosing on study days 14 and 21 |

Neuropathic pain inducement was done by following principles of Chung induced model. The SD rats were anesthetized using ketamine/xylazine sodium. The rats were shaved and placed in prone position for surgery. The L5-L6 spinal nerves were surgically litigated. The rats were returned to their cages for recuperation and recovery under comfortable warm conditions using heat lamps.

After seven days of surgery a pre selection was performed. Animals that indicate signs of post operative pain were to be selected to proceed. Pain is detected by observing when one or more of the criteria are met as follows. Licking of the operated paw, accompanied by gentle biting or pulling on the nails with the mouth; placing the leg in the air; bearing weight on the side contra-lateral to the nerve injury; deformities of the hind paw and abnormal posture and walking; weakness of the left hind paw. The animals that exhibited these pain occurring symptoms were chosen for further steps. However, the animal must be able to move its leg to ensure that the $L_4$ spinal nerve is intact. If the animal cannot move its leg, it was excluded from the study.

Second level of selection of the rats was done on day 14 after the surgery. Von Frey test was performed on the preselected rats after day 7 on day 14. Using Von Frey methodology, animals with a pain threshold of $\leq 26$ g for the operated leg will be included in the study. After this selection step, the animals were randomly placed into their experimental groups.

Blank, positive control and test compound: Blank was just the medium used for dissolving other compounds. The positive control was Gabapentin and the test compound was the final compound of formula 1 discussed in the instant disclo- On day 14 blank compound and final compound will be administered once daily starting on study day 14 through study day 21. Gabapentin, the positive control, will be administered 2 hours prior to pain testing on study days 14 and 21. The Von Frey test was be performed prior to final compound administration (pre-final compound injection) and after final compound administration at 0.5 hours, 2 hours and 4.5 hours post-final compound injection on study days 14 and 21. Additionally, if the Von Frey response for the operated leg of one of the six treatment groups is significant at 4.5 hours, all the groups will be tested again at 6.5 hours. In all instances, unless decided otherwise in the course of the study, all dosing solutions are applied as once a day intra peritoneal (IP) administration on each of the repeated dosing sessions. After the termination of the study the animals were euthanized.

Pain Response Evaluation: Pain response was evaluated using Von Frey test for mechanical allodynia. The Von Frey test for mechanical allodynia is based on applying short pulses of pressure that are not painful to a naïve animal. In fact, in order to achieve paw withdrawal from a naïve animal, the pressure applied is sometimes higher than 60 g. This often requires the researcher to apply enough pressure with the Von Frey filament to actually lift the paw of the naïve animal. However, in disease conditions, the animals are sensitive to much lower pressure and experience pain as a result of a normally non-painful stimulus.

Mechanical Allodynia Evaluation (Von Frey testing): Allodynic response to tactile stimulation was assessed using the Von Frey apparatus (Touch®). The rats were placed in an enclosure and positioned on a metal mesh surface, but allowed to move freely. The rats' cabins were covered with red cellophane to diminish environmental disturbances. The test began after cessation of exploratory behavior. The set of Von Frey monofilaments provide an approximate logarithmic scale of actual force and a linear scale of perceived intensity as provided by the manufacturer of the Von Frey apparatus (Ugo Basil).

The operating principle: When the tip of a fiber of given length and diameter is pressed against the skin at right angles, the force of application increases as long as the researcher continues to advance the probe until the fiber bends. After the fiber bends, the probe continues to advance, causing the fiber to bend more, but without additional force being applied to the paw.

Below is a table 8 showing the force (g) and its corresponding size of monofilaments.

The baseline average force required to induce a withdrawal response for the left operated leg of the Vehicle-treated animals (Group 1) was 60.00±0.00 g. On study day 14 prior to treatment, the withdrawal force of the left leg was significantly lower than the baseline measurement indicating the presence of mechanical allodynia (10.15±1.01 g; p<0.05 vs. baseline). On study day 21 prior to treatment, mechanical allodynia was still present (8.31±0.89 g; p<0.05 vs. baseline).

Positive control, gabapentin, at a dose of 150 mg/kg (Group 6) was significantly effective in reducing mechanical

| Size | 1.65 | 2.36 | 2.44 | 2.83 | 3.22 | 3.61 | 3.84 | 4.08 | 4.17 | 4.31 | 4.56 | 4.74 | 4.93 | 5.07 | 5.18 | 5.46 | 5.88 | 6.10 | 6.45 | 6.65 |
|---|---|---|---|---|---|---|---|---|---|---|---|---|---|---|---|---|---|---|---|---|
| Force (g) | 0.008 | 0.02 | 0.04 | 0.07 | 0.16 | 0.40 | 0.60 | 1.00 | 1.40 | 2.00 | 4.00 | 6.00 | 8.00 | 10 | 15 | 26 | 60 | 100 | 180 | 300 |

Rodents exhibit a paw withdrawal reflex when its paw is unexpectedly touched. The Touch Test™ Sensory Evaluator can be used on the plantar surfaces of the rat's foot. The animal will indicate sensation by pulling back its paw. The minimal force needed to elevate the withdrawal reflex is designated/considered as the value of reference.

Body Weights: Body weight was measured starting on study day-1 for baseline values and again, seven days after the surgery (study day 7). In addition, animals that demonstrated criterion for mechanical allodynia on study day 14 were also weighed after selection and grouping on study day 14 and again, on day 21.

STATISTICS/DATA EVALUATION: All data are presented as means±SEM. The values were analyzed using a one-way ANOVA following by a Tukey post-test (GraphPad Prism) to compare the Vehicle group (Group 1) and positive control group, gabapentin, (Group 6) to each treatment at each time point. A p value <0.05 is considered to represent a significant difference.

Figure 4:
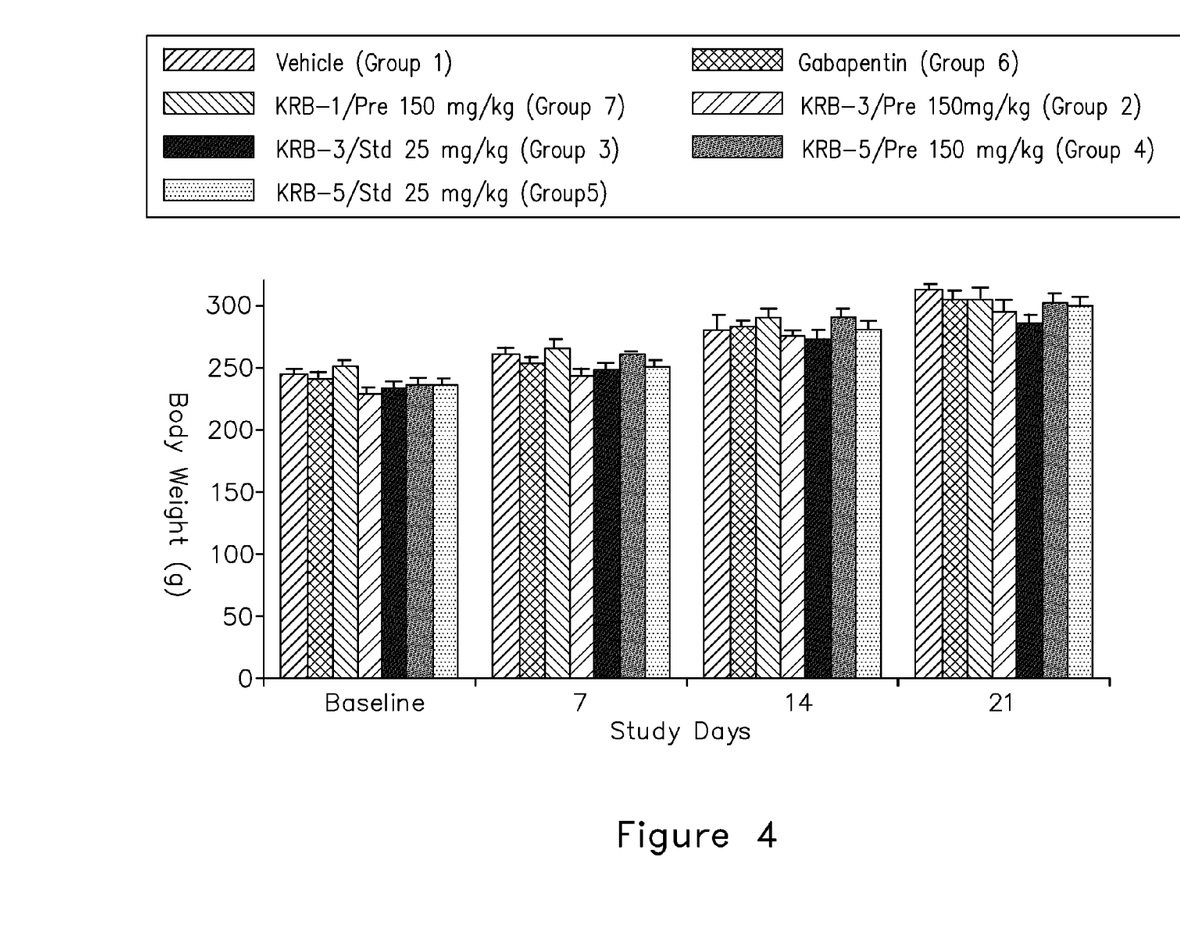
FIG. 4 shows the body weight changes during the course of treatment for up to 21 days.

Body Weight: All animals gained weight during the study, which indicated good general health throughout the study. There were no significant differences in weight gain between the groups. At baseline (day −1), the mean body weight for all animals was 240.65±1.38 g.

Body weights were also measured on study days 7, 14, and 21. At study day 7, the mean body weight for all groups was 256.38±1.74 g. At study day 14, the mean body weight for all groups was 283.45±2.57 g. At study termination (day 21), the mean body weight was 302.61±2.48 g.

Figure 5:
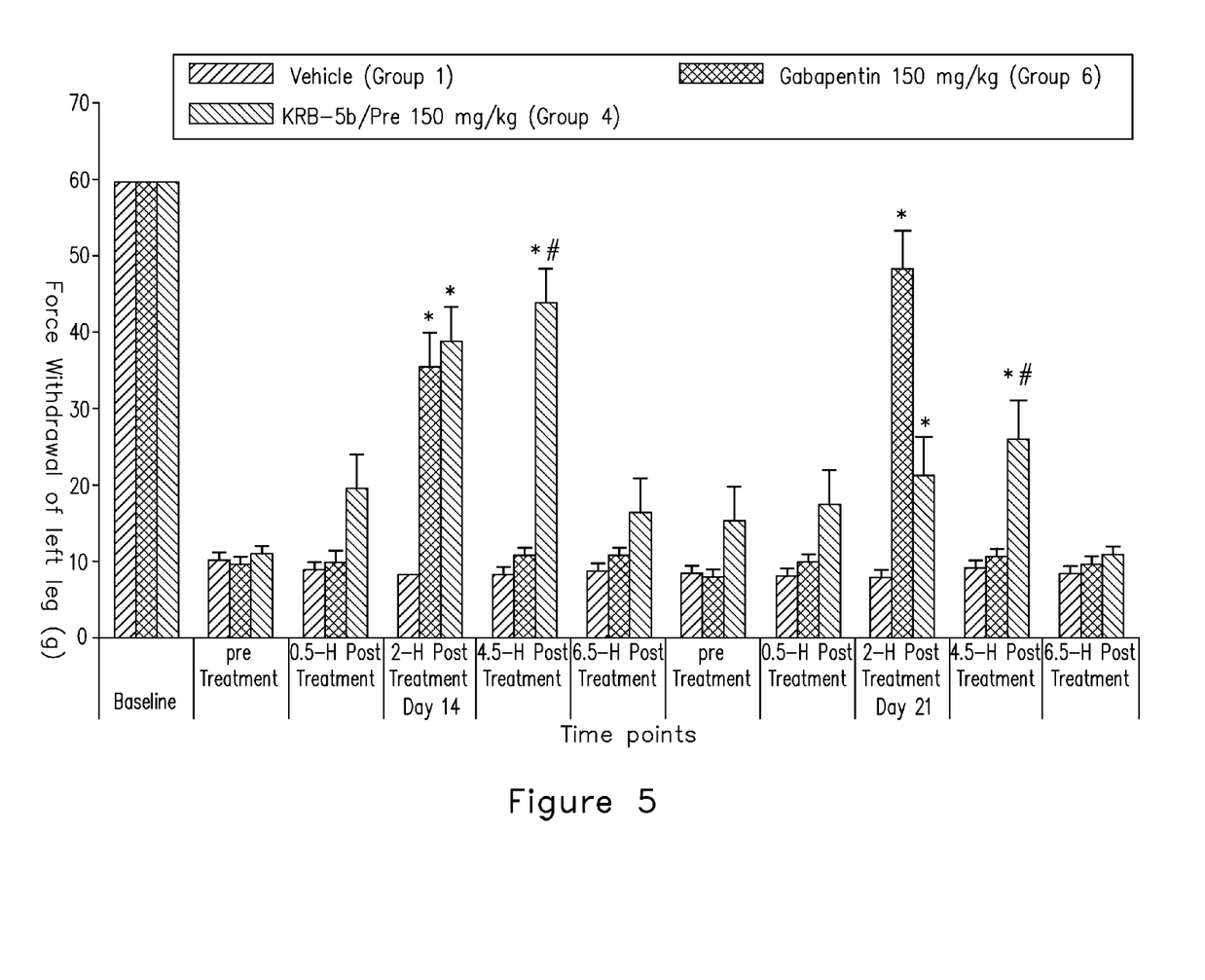
FIG. 5 displays comparative results of the compound, blank and the Gabapentin dose for pain induced rats as mean Von frey force of KRB5B/Pre required for withdrawal of left operated leg (g).

Von Frey Test: Results are presented as the mean force (g) required to induce a withdrawal response for the left operated leg. Mechanical allodynia was observed as an increase in the animal sensitivity to the Von Frey filaments at different time points on study days 14 and 21 (0.5 hr, 2 hr, 4.5 hr and 6.5 hr post treatment).

allodynia on day 14 at 2 hours post-treatment compared to the Vehicle group: 35.69±5.69 g vs. 8.15±0.36 g for the Vehicle (p<0.05).

Gabapentin was also significantly effective at reducing mechanical allodynia at 2 hours post treatment on study day 21 compared to the Vehicle: 48.69±4.96 g vs. 7.85±0.48 g for the Vehicle (p<0.05).

KRB-5b at a dose of 150 mg/kg (Group 4): On study day 14 at 2 hours post-treatment, KRB-5b at a dose of 150 mg/kg was significantly effective in reducing mechanical allodynia compared to the Vehicle-treated group: 39.00±7.19 g vs. 8.15±0.36 for the Vehicle (p<0.05).

This analgesic effect continued to be significant compared to the Vehicle group at the 4.5 hours post-treatment time point: 44.20±6.55 g vs. 8.38±0.73 g for the Vehicle (p<0.05). In fact, the Von Frey response of KRB-5b expressed greater analgesic activity than gabapentin at this time point, as expressed by a greater force required for withdrawal: 44.20±6.55 g vs. 10.69±1.42 g for gabapentin (p<0.05).

On study day 21 at 4.5 hours post-treatment, KRB-5b was significantly effective in reducing mechanical allodynia compared to the Vehicle-treated group: 26.20±5.81 g vs. 9.08±0.86 for the Vehicle (p<0.05). At this time point, the Von Frey response of KRB-5b was significantly more effective than positive control, gabapentin, as indicated by the greater force required for withdrawal: 26.20±5.81 g vs. 10.62±0.90 g for gabapentin (p<0.05).

CONCLUSIONS: Test Item KRB-5b compound of formula 1, at a dose of 150 mg/kg was effective as a pain analgesic item as based on the mechanical allodynia results at 2 and 4.5 hours post-treatment on study day 14 and at 4.5 hours on study day 21 compared to the Vehicle-treated animals. Treatment with KRB-5b demonstrates prolonged analgesic activity compared to gabapentin, which was active only at 2 hours post dosing.

TABLE 9

The mean Von Frey force required for withdrawal of left operated leg on study day 14 (g).

| | | | | | | | Day 14 | | | | | | |
|---|---|---|---|---|---|---|---|---|---|---|---|---|---|
| | | Baseline | | Pre-treatment | | 30 min Post treatment | | 2 hr Post treatment | | 4.5 hr Post treatment | | 6.5 hr Post treatment | |
| Group No. | Treatment | MEAN | SEM | MEAN | SEM | MEAN | SEM | MEAN | SEM | MEAN | SEM | MEAN | SEM |
| 1 | Vehicle | 60.00 | 0.00 | 10.15 | 1.01 | 8.85 | 0.68 | 8.15 | 0.36 | 8.38 | 0.73 | 8.69 | 0.67 |
| 6 | Gabapentin | 60.00 | 0.00 | 9.69 | 1.07 | 9.85 | 1.62 | 35.69* | 5.69 | 10.69 | 1.42 | 10.69 | 1.03 |

TABLE 9-continued

The mean Von Frey force required for withdrawal of left operated leg on study day 14 (g).

| Group | | Baseline | | Pre-treatment | | Day 14 | | | | | | | |
|---|---|---|---|---|---|---|---|---|---|---|---|---|---|
| | | | | | | 30 min Post treatment | | 2 hr Post treatment | | 4.5 hr Post treatment | | 6.5 hr Post treatment | |
| No. | Treatment | MEAN | SEM | MEAN | SEM | MEAN | SEM | MEAN | SEM | MEAN | SEM | MEAN | SEM |
| 4 | KRB-5b 150 mg/kg | 60.00 | 0.00 | 11.00 | 1.15 | 19.60 | 5.20 | 39.00* | 7.19 | 44.20*# | 6.55 | 16.40 | 2.61 |

*$p < 0.05$ vs. Vehicle,
$p < 0.05$ vs. Gabapentin

TABLE 10

The mean Von Frey force required for withdrawal of left operated leg on study day 21 (g).

| Group | | Baseline | | Pre-treatment | | Day 21 | | | | | | | |
|---|---|---|---|---|---|---|---|---|---|---|---|---|---|
| | | | | | | 30 min Post treatment | | 2 hr Post treatment | | 4.5 hr Post treatment | | 6.5 hr Post treatment | |
| No. | Treatment | MEAN | SEM | MEAN | SEM | MEAN | SEM | MEAN | SEM | MEAN | SEM | MEAN | SEM |
| 1 | Vehicle | 60 | 0 | 8.31 | 0.89 | 7.92 | 0.75 | 7.85 | 0.48 | 9.08 | 0.86 | 8.31 | 0.50 |
| 6 | Gabapentin | 60 | 0 | 7.92 | 0.72 | 9.85 | 1.60 | 48.69* | 4.96 | 10.62 | 0.90 | 9.62 | 0.96 |
| 4 | KRB-5b 150 mg/kg | 60 | 0 | 15.40 | 2.44 | 17.50 | 2.46 | 21.30# | 4.79 | 26.20*# | 5.81 | 10.80 | 1.14 |

*$p < 0.05$ vs. Vehicle,
$p < 0.05$ vs. Gabapentin

A one-way ANOVA following by a Tukey post-test was performed to determine significance of treatment effects compared to the blank. A p value <0.05 is considered to represent a significant difference.

The instant final compound of formula 1 at a dose of 150 mg/kg was effective in treating the spinal nerve ligation model for neuropathic pain in rats as reflected in the parameters of mechanical allodynia at 2 hours post-treatment on study days 14 and 21. The activity of the instant final compound of formula 1 at a dose of 150 mg/kg was similar to the activity of Gabapentin, the positive control in this study.

The present disclosure provides among other things compound, method to synthesize the compound for formula 1 and treating pain in mammals using the compound of formula 1. While specific embodiments of the subject disclosure have been discussed, the above specification is illustrative and not restrictive. Many variations of the compounds, compounds and methods herein will become apparent to those skilled in the art upon review of this specification.

Accordingly, the specification and drawings are to be regarded in an illustrative rather than a restrictive sense.

INDUSTRIAL APPLICABILITY

There are multiple applications for compound of formula 1, compound of formula 1 with pharmaceutically acceptable additives to treat mammals suffering from pain, more specifically neuropathic pain in general. These compounds may be used in the treatment of diseases related to pain and its related complications.

What is claimed is:
1. A compound, comprising of formula 1:

2. The compound of claim 1, further comprising:
a pharmaceutically acceptable salt form of compound of formula 1

3. A method of treating pain, comprising:
administering the compound of formula 1 as shown below to a patient suffering from a disease wherein the disease is at least one of a chronic disease, chronic disorder, hematological disease, inflammation, orthopedic disease, cardiovascular disease, renal disease, skin disease, neurological disease, metastasis disease and ocular complications.

4. The method of treating pain of claim 3, wherein administering is at least one of a non-invasive peroral, topical, enteral, gel, syrup, lotions, healing pads, transmucosal, targeted delivery, sustained release delivery, delayed release, pulsed release, patch and parenteral methods.

5. A method of making the compound of formula 1, comprising:
adding the solution of 2, 6 xylidine dissolved in dichloromethane and chloroacetyl chloride for 30 minutes at 0° C. to make a mixture;
raising the temperature of the mixture and stirring it overnight for a reaction to obtain a reaction mixture;
monitoring the completion of the reaction by thin layer chromatography;
washing the reaction mixture with water followed by washing with brine solution;
separating an organic and an inorganic layer from the reaction mixture;
drying the organic layer over anhydrous $Na_2SO_4$ as a solid;
evaporating the remaining liquid to get a dry solid;
recrystallizing the dry solid using a hexane; and
filtering a recrystallized dried material to yield a compound 2

6. The method of making the compound of formula 1 as in claim 5, further comprising:
adding ethyl amine solution in tetrahydrofuran to dissolve the compound 2:

stirring for four hours to dissolve the compound 2 in tetrahydrofuran;
monitoring the reaction by thin layer chromatography;
concentrating the reaction mixture under pressure;
recrystallizing the dried solid in ethyl acetate; and
filtering the recrystallized solid and drying the solid to yield a compound 3:

7. The method of making the compound of formula 1 as in claim 6, further comprising:
mixing N,N-dimethyl formamide, potassium carbonate and methyl chloroacetate at room temperature by continuously stifling to the compound 3 monitoring the progress of the reaction by thin layer chromatography;
adding ethyl acetate and water to separate an organic layer and an inorganic layer;
washing the organic layer using brine solution;
drying the organic layer over $Na_2SO_4$ and evaporated under reduced pressure; and eluting a compound 5 using column chromatography.

8. The method of making the compound of formula 1 as in claim 7, further comprising:
mixing a lithium aluminum hydride solution, tetrahydrofuran and the compound 5 for 2 hours at room temperature to obtain a reaction mixture;
quenching the reaction mixture with a saturated ammonium chloride;

extracting an organic layer using ethyl acetate; and
evaporating and drying the organic layer over an anhydrous Na$_2$SO$_4$ to yield a compound 6

9. The method of making the compound of formula 1 as in claim 8, further comprising:
stirring a mixture of a DCM, EDCI, lipoic acid and the compound 6 for 24 hours at room temperature to obtain a reaction mixture;
diluting the reaction mixture using the DCM and a brine solution;
drying and evaporating the reaction mixture over Na$_2$SO$_4$; and
purifying the dried reaction mixture using column chromatography to obtain a compound of formula 1 as a pale yellow semi-solid.

10. A kit, comprising:
a pharmaceutical composition of formula 1 and an instruction for using the compound for treatment of pain.

* * * * *